United States Patent [19]

Gordon et al.

[11] Patent Number: 5,120,502
[45] Date of Patent: Jun. 9, 1992

[54] PRESSURE RELIEF VALVE FOR MEMBRANE OXYGENATOR

[75] Inventors: Lucas Gordon, The Woodlands, Tex.; Victor Ham, Tustin, Calif.

[73] Assignee: Baxter International Inc., Deerfield, Ill.

[21] Appl. No.: 617,922

[22] Filed: Nov. 21, 1990

Related U.S. Application Data

[63] Continuation of Ser. No. 179,708, Apr. 11, 1988, abandoned.

[51] Int. Cl.⁵ .............................................. A61M 1/14
[52] U.S. Cl. ......................................... 422/48; 422/46; 422/113; 128/DIG. 3; 261/DIG. 28; 210/321.72; 210/321.81
[58] Field of Search ..................... 422/46, 48, 113, 45, 422/47; 128/DIG. 3; 261/DIG. 28; 210/321.72, 321.81, 321.91

[56] References Cited

U.S. PATENT DOCUMENTS

| | | | |
|---|---|---|---|
| 3,856,475 | 12/1974 | Marx | 422/113 X |
| 4,196,075 | 4/1980 | Bentley | 422/48 X |
| 4,400,401 | 8/1983 | Beauvais et al. | 422/113 X |
| 4,424,190 | 1/1984 | Mather, III et al. | 422/48 X |
| 4,620,965 | 11/1986 | Fukasawa et al. | 422/46 |
| 4,698,207 | 10/1987 | Brigham et al. | 210/321.72 X |
| 4,734,269 | 3/1988 | Clarke et al. | 128/DIG. 3 |
| 4,889,693 | 12/1989 | Su et al. | 422/310 X |

*Primary Examiner*—Lynn M. Kummert
*Attorney, Agent, or Firm*—Michael C. Schiffer; Bruce M. Canter; Robert D. Buyan

[57] ABSTRACT

A membrane oxygenator having a gas pressure relief valve operable to release gas when the gas pressure in the oxygenator exceeds a predetermined level. Generally, the membrane oxygenator includes a housing in which is mounted a gas-permeable, liquid-impermeable membrane, i.e. a bundle of microporous hollow fibers. This membrane defines separate oxygen enrichable fluid and gas flow pathways. The housing also includes both gas and oxygen enrichable fluid inlet and outlet ports communicating with respective opposite ends of the gas and oxygen enrichable fluid flow pathways. The gas pressure relief valve communicates with the gas flow pathway.

22 Claims, 3 Drawing Sheets

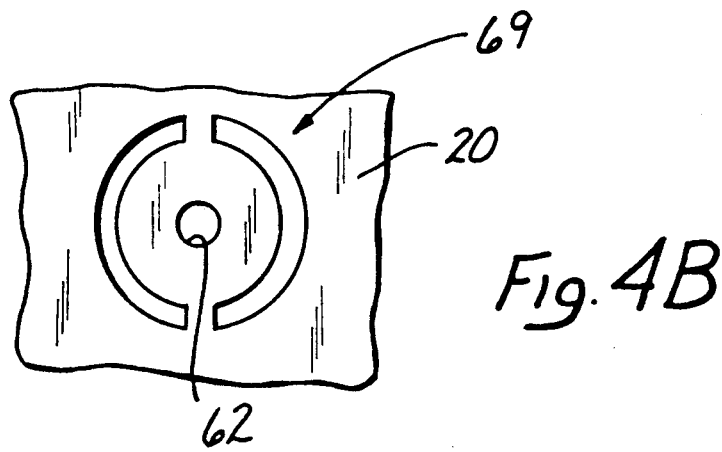
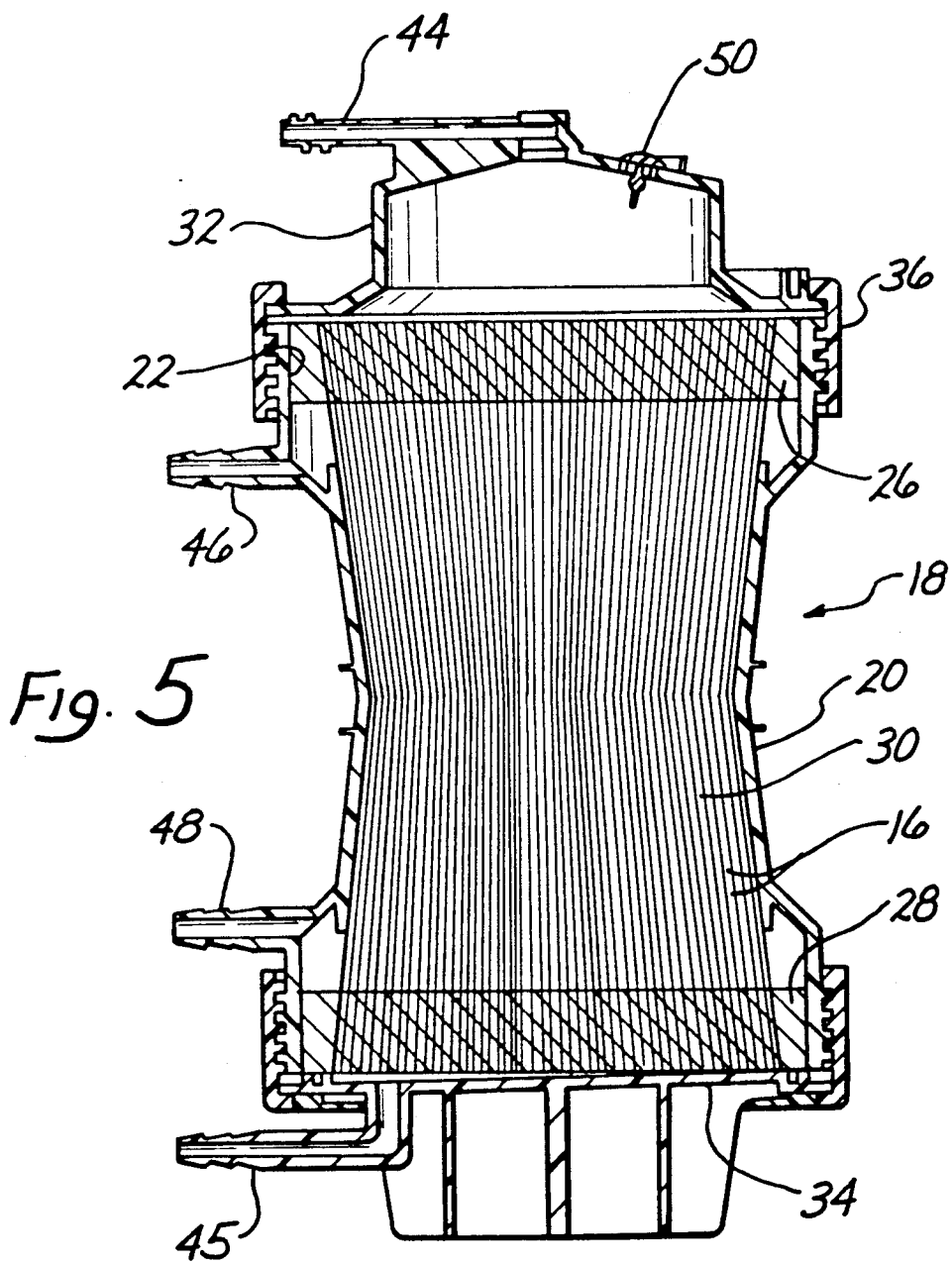

PRESSURE RELIEF VALVE FOR MEMBRANE OXYGENATOR

This is a continuation of co-pending application Ser. No. 07/179,708 filed on Apr. 11, 1988 now abandoned.

BACKGROUND OF THE INVENTION

The present invention relates to devices for oxygenating oxygen enrichable fluid, e.g. blood, and in particular to gas-permeable, liquid-impermeable membrane oxygenators having a gas pressure relief valve.

During cardiovascular surgery, oxygenators and other types of devices are utilized to carry out the function of the patient's heart and lungs. While various types of oxygenators are known, the basic two types of oxygenators are the bubble oxygenators and the gas-permeable, liquid-impermeable membrane oxygenators. Bubble oxygenators function by bubbling an oxygen bearing gas into the blood. Membrane oxygenators perform the transfer of oxygen and carbon dioxide between the blood and an oxygen rich gas across a gas-permeable, liquid-impermeable membrane.

In particular, membrane oxygenators include a gas-permeable, liquid-impermeable membrane mounted in a housing to define separate blood and gas flow pathways. The membrane selectively allows passage of molecular oxygen and carbon dioxide, while preventing the transfer of fluid, i.e. water. The transfer of the oxygen and carbon dioxide across the membrane occurs because of the concentration difference between these gases in the oxygen-depleted blood and oxygen rich gas, which transfer is known as diffusion.

While it is desirous to effect the transfer of oxygen and carbon dioxide, the pressure of the oxygen enriched gas must be maintained low enough to inhibit the forcing of large quantities of the gas through the membrane. Such an increase may occur if the gas outlet port becomes occluded for any reason. When the gas side pressure exceeds the blood side pressure, gross size bubbles of the gas will be forced into the blood side fluid pathway. These bubbles present the danger of stroke or even death to the patient when they pass from the oxygenator into the patient's blood stream.

One particular known membrane oxygenator employs a plurality of hollow microporous fibers as the gas-permeable, liquid-impermeable membrane. These hollow fibers are arranged in a bundle mounted in the housing. The fibers are arranged to position the respective opposite open end of each fiber at either end of the housing. Each respective housing end is formed with a cavity isolated from the main internal housing cavity. Thus a fluid flow pathway is formed by the combination of these cavities and the interior of the multiple fibers. The blood or oxygen rich gas is passed through this defined flow pathway, while the other is passed through the main housing cavity, which defines a separate fluid flow pathway.

The release of excess gas to reduce the pressure in the gas flow pathway has heretofore not been performed with membrane oxygenators using pressure relief valves. Typical procedures for maintaining the gas pressure within an exceptable range involves a careful monitoring and control of the gas pressure. Furthermore, oxygenators have been designed which merely vent excess gas to the atmosphere. These types of oxygenators isolate the blood from the atmosphere by passing the blood through the hollow fibers forming the gas-permeable, liquid-impermeable membrane.

The main disadvantage with oxygenators having such vents pertains to a procedure used to prime the oxygenator prior to introduction of the blood. Generally, such procedure involves flushing the interior of the oxygenator with carbon dioxide gas. The carbon dioxide gas removes any gas in the oxygenator prior to the introduction of the blood. The major disadvantage with such vented oxygenators is that the carbon dioxide gas escapes during the flushing procedure, and does not provide any beneficial flushing of the oxygenator.

It can thus be seen that it would be highly desirable to provide an oxygenator which has a means for regulating the gas pressure without the above described disadvantages.

SUMMARY OF THE INVENTION

The present invention is directed to a membrane oxygenator. This oxygenator includes a gas pressure relief valve operable to release gas when the gas pressure in the oxygenator exceeds a predetermined level. However the valve operates in such a manner to ensure that a sufficient amount of carbon dioxide gas passes through the oxygenator during the flushing procedure.

Generally the oxygenator includes a housing in which is mounted a gas-permeable, liquid-impermeable membrane, i.e. a bundle of microporous hollow fibers. This membrane defines separate oxygen enrichable fluid, i.e. blood and gas flow pathways. The housing also includes both gas and blood inlet and outlet ports communicating with respective gas and blood flow pathways.

In accordance with the invention, the housing of the oxygenator is fitted with at least one pressure relief valve which communicates with the gas flow pathway. This pressure relief valve is operable when the gas pressure in the gas flow pathway reaches a predetermined level to release gas from the flow pathway. The valve releases enough gas to minimize the potential of large quantities of the gas being forced directly into the blood flow pathway through the membrane. The pressure relief valve further operates during the preliminary flushing procedure to ensure that a sufficient amount of the carbon dioxide gas passes through the oxygenator.

In accordance with a preferred embodiment the blood flow pathway is defined by a plurality of individual fibers mounted as a bundle in the housing. The opposite open ends of each fiber is embedded within a sealing material, which also seals the ends of the housing. This sealing material thus forms the gas flow pathway inside the housing about the fibers. The open ends of the fibers remain exposed, with a cap affixed to each respective end of the housing to define separate cavities. Each cavity communicates with the open ends of the fibers. Both of these separate cavities, in combination with the interiors of the individual hollow fibers defines the blood flow pathway. Ports are appropriately connected to both of the flow pathways.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIGS. 4A and 4B are front views of other aperture configurations for pressure relief valves of the invention; and FIG. 5 is a side partially sectioned view of an oxygenator incorporating the pressure relief valve of FIG. 2 in accordance with another embodiment of the invention.

DESCRIPTION OF THE INVENTION

Figure 1:
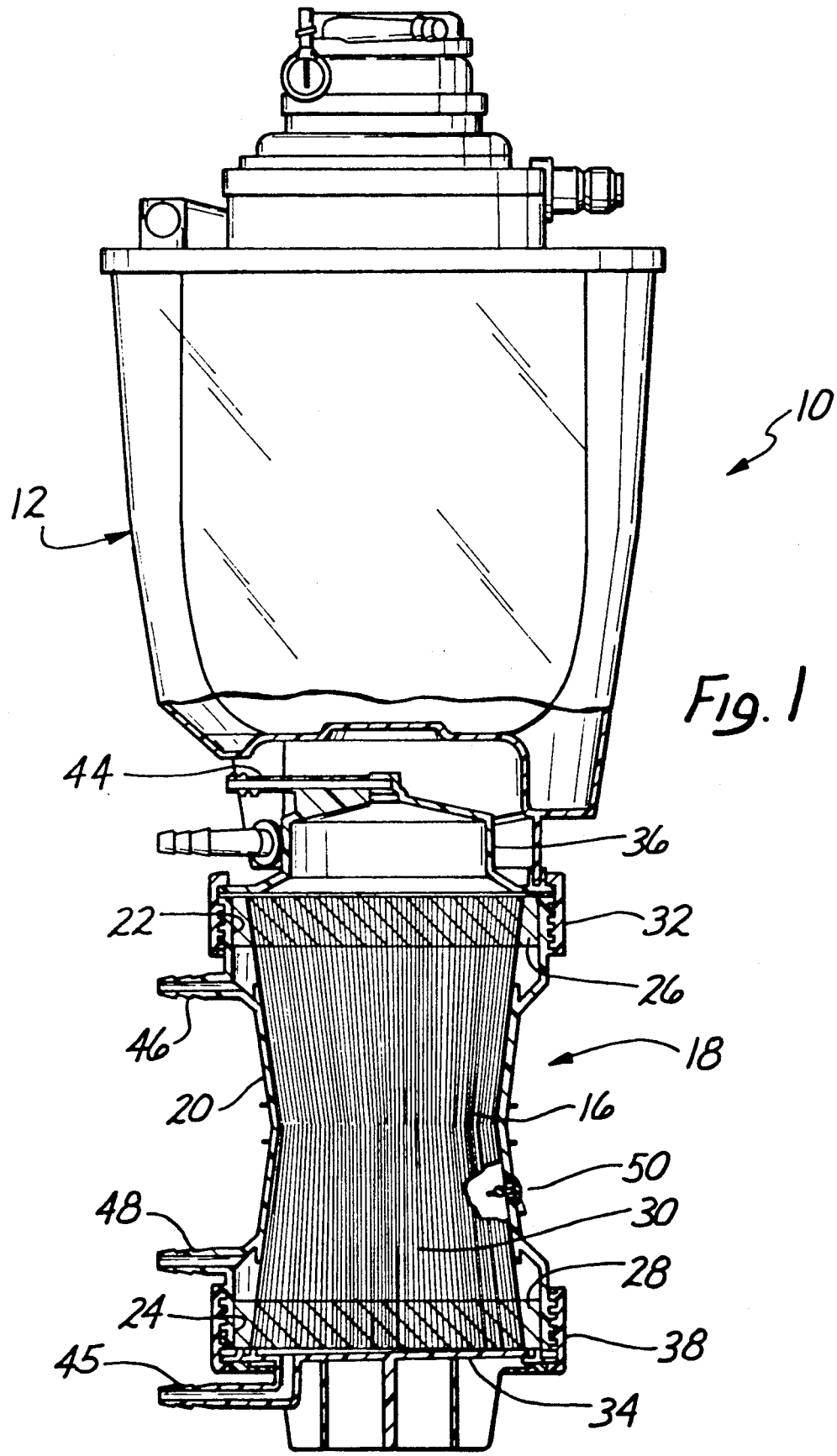
FIG. 1 is a side, partially sectioned view of a blood oxygenator/heat exchanger and reservoir device incorporating the gas pressure relief valve of the invention.

The present invention is directed to membrane oxygenators which provide for the diffusion of molecular gas, e.g. oxygen and carbon dioxide, between an oxygen enrichable fluid, i.e. blood, and an oxygen enriched gas. In particular, the invention is directed to membrane oxygenators which replace the function of the heart and lungs during cardiac surgery. In particular, the present invention is directed to membrane oxygenators including a gas pressure relief valve.

Generally, membrane oxygenators include a housing in which a gas-permeable, liquid-impermeable membrane is mounted to define two fluid flow pathways. Examples of typical oxygenators are disclosed in U.S. Pat. No. 4,151,088; U.S. Pat. No. 4,376,095; U.S. Pat. No. 4,424,190; and U.S. Pat. No. 4,451,562. A first fluid flow pathway carries the blood, while the second fluid flow pathway carries oxygen enriched gas. The membrane allows passage of oxygen and carbon dioxide between the two fluids, while preventing the passage of any liquid.

This membrane will under normal operating conditions prevent passage of large quantities of the gas directly into the blood side fluid. However, under certain conditions, such as misuse or occlusion of the gas outlet, large gas quantities may be forced through the membrane. This causes formation of gas bubbles in the blood side fluid flow. Gas bubbles entering the blood side fluid flow increases the potential of the bubbles entering the patient's blood stream which will cause a stroke or even death of the patient.

While the present invention may be utilized with any suitable membrane oxygenator, the preferred oxygenator, which the invention will be described in conjunction with, is that oxygenator wherein the membrane is defined by a bundle of microporous hollow fibers.

That is, a bundle of hollow fibers is mounted in an oxygenator housing, with the interiors of the individual hollow fibers defining one of the fluid pathways, preferably the blood flow pathway. The opposite open ends of each fiber are embedded in a material which seals off the ends of the housing to define a main cavity inside the housing. The fiber open ends remain exposed outside the housing, with a cap secured to the respective housing ends to define separate cavities. The fiber open ends communicate with the respective separate cavity. The main housing cavity defines the other fluid flow pathway, preferably the gas flow pathway. The oxygenator further includes various inlet and outlet ports which communicate with the two flow pathways.

As stated, the oxygenators of the invention further include a gas pressure relief valve. This valve is mounted to a wall of the oxygenator housing and communicates with the gas flow pathway. The valves suitable for the invention include a resiliently deflectable flap mounted to the oxygenator housing wall. This flap covers one or more apertures formed in the associated oxygenator housing wall.

The valve is designed to maintain the flap against the housing wall until the pressure of the gas in the housing, and specifically the gas carrying pathway exceeds a predetermined level. When the pressure exceeds this level the gas forces the flap away from the wall allowing a sufficient amount of the gas to escape through the apertures. This lowers the gas pressure below the predetermined level. The predetermined level is selected to remain equal to or below the fluid pressure of the blood flowing through the other flow pathway.

Referring more particularly to FIG. 1, a blood oxygenator/heat exchanger and reservoir is seen generally at 10. The oxygenator/heat exchanger and reservoir 10 is of the type described and claimed in U.S. Pat. No. 4,698,207, which is assigned to the same assignee as the instant application, and which description is incorporated herein by reference. Accordingly, the oxygenator/heat exchanger and reservoir 10 will not be described in any detail herein.

Generally, the oxygenator 10 includes a heat exchanger 12 mounted atop the oxygenator portion 14. The heat exchanger 12 may have any suitable construction, and for that matter is not critical to the invention. While the oxygenator portion 14 has that construction as described in the incorporated patent, other suitable constructions may be substituted.

In the illustrated embodiment the gas-permeable, liquid-impermeable membrane is defined by a plurality of microporous hollow fibers, as seen generally at 16. These fibers 16 are arranged in a bundle and mounted in a housing, seen generally at 18. Housing 18 is defined by a cylindrical side wall 20, which is open at opposite ends 22 and 24.

The hollow fibers may be prepared in accordance with any suitable technique, from any appropriate gas permeable material, e.g. polypropylene, polyethylene or other polyolefin material. The respective open ends of the fibers 16 are fixed in a material, typically a urethane material, to seal the housing open ends 22 and 24, as seen as seals 26 and 28. These seals 26 and 28 define an internal housing cavity, seen at 30. The open ends of the respective fibers 16 remain exposed outside of these seals 26 and 28.

The exposed open ends of the fibers 16 are isolated by securing respective caps to the opposite open housing ends 22 and 24, which caps are seen respectively at 32 and 34. These caps 32 and 34 are secured to the housing 18 using inwardly threaded collars 36 and 38, respectively, which threadably engage outwardly disposed threads formed about the outer surface of the housing 18 adjacent to the open housing ends 22 and 24. The caps 32 and 34 form cavities, seen at 40 and 42, which communicate with the interiors of the hollow fibers 16.

Thus a first fluid flow pathway is defined by these cavities 40 and 42 and the interiors of the hollow fibers 16. A second fluid flow pathway is defined by the housing interior cavity 30.

Entrance and exit to these fluid flow pathways is obtained through various inlet and outlet ports, with an inlet port 44 and outlet port 45 being for the first fluid flow pathway, and an outlet and inlet ports for the second fluid flow pathway being seen at 46 and 48, respectively.

The oxygenator 14 includes a gas pressure relief valve, seen generally at 50. This valve is mounted to the side wall 20, and controls the communication between the second fluid flow pathway and the exterior of the oxygenator 14.

The valve 50, which will be more fully described herein, is generally constructed to facilitate mounting to the housing side wall 20 and includes a resiliently deflectable flap portion. This flap portion is constructed from a suitable material to ensure that under normal load conditions the flap will lie against the side wall 20. In this position the flap will cover one or more apertures, not seen in FIG. 1, formed in the side wall 20.

However, under certain conditions the pressure of the gas in the second fluid pathway, or cavity 30, may build up to such a level that the flap portion of the valve is moved away from the side wall 20 allowing for the escape of gas. This will continue until a sufficient amount of gas has escaped to lower the pressure within the second flow pathway.

Again the type of material from which the valve is formed, and in particular the flap portion, will directly effect the movement of the flap. It is thus desirable that this material be rigid enough to normally lie against the side wall, while possessing sufficient elasticity and memory to ensure that the flap can be forced away from the side wall, but will return back against the wall 20 after a sufficient amount of the gas has escaped to lower the pressure in the interior cavity 30, or second flow pathway.

Any suitable construction may be used provides a flap portion as described above. Examples of such valves include diaphragm, duck billed, umbrella, slit and hinged valves. The more preferred embodiment is an umbrella valve which has been found to provide particularly good venting ability.

Figure 2:
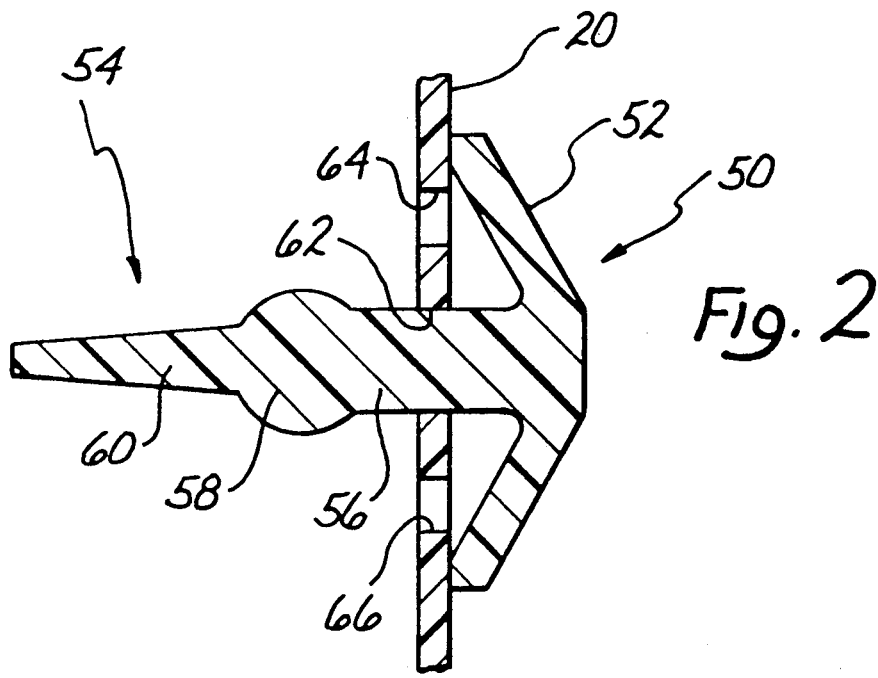
FIG. 2 is a cross-sectional view of the gas pressure relief valve seen in FIG. 1.

Referring to FIG. 2 the preferred valve 50 will be described in greater detail. As seen, valve 50 is mounted to the side wall 20. Valve 50 includes a circular canopy 52, out from which extends a projection, seen generally at 54. This projection 54 is formed with a centrally located stem 56, a bulbous portion 58 and a tapered shaft 60.

The projection 54 is used to affix the valve 50 to the side wall 20. In particular, the side wall 20 includes a mounting hole 62, through which can be pulled the projection 54. In this regard the hole 62 is dimensioned to easily receive the tampered shaft 60, but is narrower than the bulbous portion 58. As a result, the bulbous portion 58 must be forceably pulled through the hole 62.

Since the valve 50 is formed from a resiliently deflectable material, typically a natural or synthetic rubber, the bulbous portion 58 can be pulled through the hole 62 to lock the valve 50 to the side wall 20. In order to enhance this lock, and also to provide the valve 50 with a degree of tensile force, the width of the side wall 20 is greater than the length of the centrally located stem 56. More specifically, the thickness of the wall at the location at which the valve is affixed will influence the tension on the valve. In accordance with a preferred embodiment the wall thickness will be from about 0.080 inches to about 0.090 inches, and preferably about 0.085 inches. Thus when the bulbous portion 58 is pulled through the hole 62 this centrally located stem 56 is stretched, and will remain stretched.

The tension on the valve 50 is enhanced by forming the circular canopy 52 to define an angle with the axis of the projection 54 of less than ninety degrees. By forming the valve 50 from an elastic material, and by ensuring that the centrally located stem 56 is stretched when pulled through the hole 62 the peripheral edge of the canopy 52 exerts a force against the side wall 20. That is, the mounting of the valve 50 to the side wall 20, by pulling the projection 54 through the hole 62 causes the peripheral edge of the canopy 52 to press against the side wall 20.

In order to enhance this tension the thickness of the canopy 52 should be at least about 0.008 inches, preferably from about 0.008 inches to about 0.017 inches. This thickness provides the necessary strength to the canopy 52 as it is brought to rest against the side wall 20.

Figure 3:
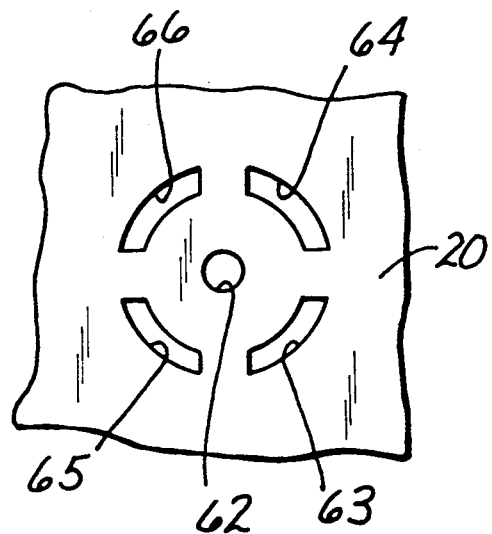
FIG. 3 is a front view of an aperture configuration for the pressure relief valve of FIG. 2.
Figure 4A:
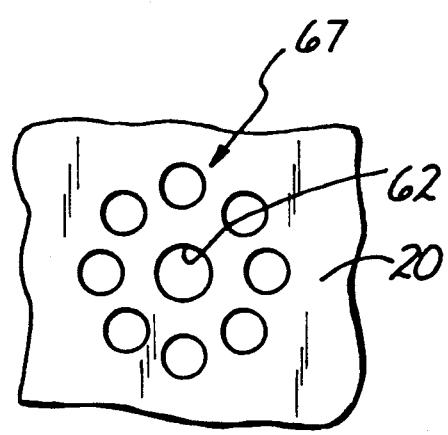

As stated the canopy 52 is large enough to cover one or more apertures formed in the side wall 20. In the embodiment seen in FIG. 2, four circular or arched shaped apertures are formed at opposing sides of the hole 62. This embodiment is better seen in FIG. 3, with the four circular apertures seen at 64 through 66. However, other aperture arrangements may be substituted for this arrangement, with two such arrangements shown in FIGS. 4A and 4B. The hole through which the projection 54 is pulled is labeled 62, while the arrangement of apertures which may be substituted for circular apertures 64 through 66 are generally referenced at 67 in FIG. 4A, and 69 in FIG. 4B.

As stated, when the pressure within the interior housing cavity 30, or the second flow pathway reaches a predetermined level the canopy 52 is moved sufficiently away from the side wall 20 to allow gas to escape. This internal pressure may be fixed at any level, with the appropriate materials, and thickness of the canopy 52 being selected to provide for such level. That is, by properly selecting the materials from which the valve 50 is formed, and by selecting the proper thickness for the canopy 52, any desired pressure level may be chosen at which the gas will escape by moving the canopy 52 away from the side wall 20.

Generally, such pressure level is dependent upon that pressure at which the gas will be forced through the particular hollow fibers 16 forming the permeable membrane. Thus the proper pressure level will vary from one embodiment to another, depending upon the material, and physical characteristics of the hollow fibers. Typically, the pressure at which the valve will be operative is at least 5 millimeters of mercury (mm Hg). This allows the oxygenator 14 to be flushed with carbon dioxide in accordance with standard operating procedures.

Thus the valve 50 should at a minimum only allow gas to escape when the internal pressures in the second pathway exceed about 5 mm Hg, and preferably when the internal pressure level is from about 7 to about 16 mm Hg.

While the above description positions the valve 50 in communication with the second flow pathway, it should be noted that the valve 50 may be placed in communication with the first flow pathway, that is, the pathway defined by the interior of the hollow fibers 16 when such pathway carries the oxygen enriched gas. In this regard, reference is made to FIG. 5, wherein only a blood oxygenator 68 is seen.

In accordance with this embodiment the device does not include the heat exchanger and reservoir portion 12, as described above, and further the pressure relief valve 50 is mounted to one of the caps, i.e. cap 70, coupled to an end of the housing 72. That is, the pressure relief valve 50 communicates with that fluid flow pathway defined by the interior of the hollow fibers 16.

The remaining components of the oxygenator 68 are similar to, and have the same reference numerals as the components described above for the oxygenator portion 14 of the oxygenator/heat exchanger and reservoir 10, and thus will not be described any further herein.

While the preferred embodiments have been described, various modifications and substitutions may be made thereto without departing from the scope of the invention. Accordingly, it is to be understood that the invention has been described by way of illustration and not limitation.

What is claimed is:

1. A membrane oxygenator comprising:
   a housing defining an internal cavity;
   a gas-permeable, liquid-impermeable membrane mounted in said housing internal cavity, said membrane partitioning said housing cavity into two fluid flow pathways, with one of said pathways designed to carry a flow of oxygen enrichable fluid and the other of said pathways designed to carry an oxygen enriched gas;
   means defining fluid ports communicating with said pathways;
   at least a first one-way pressure relief valve fitted to said housing to communicate with said gas carrying fluid flow pathway, said one-way pressure relief valve being configured to prevent air from being pulled into said gas carrying fluid flow pathway while allowing gas to flow out of said gas carrying fluid flow pathway when the gas pressure within the gas carrying fluid flow pathway exceeds a predetermined pressure level.

2. The oxygenator of claim 1 wherein said pressure relief valve is structured so that said predetermined pressure is about 5 mm Hg.

3. The oxygenator of claim 2 wherein said pressure relief valve includes a flap means fitted to a side of said housing, with said housing side further defining at least a first aperture communicating with said gas carrying pathway, and wherein said flap means is formed with a first portion which is affixed to said housing side and a second portion having a resiliently deflectable flap normally covering said aperture when said gas pressure is below 5 mm Hg, and which flap is resiliently moved away from said aperture when said gas pressure exceeds 5 mm Hg.

4. The oxygenator of claim 1 wherein said pressure relief valve is structured so that said predetermined pressure is in the range of about 7 mm Hg to about 16 mm Hg.

5. The device of claim 1 wherein said one-way pressure relief valve is constructed so that said predetermined pressure level is below the pressure level of blood flowing through the blood flow pathway.

6. The device of claim 1 wherein said one-way pressure relief valve is constructed so that said predetermined pressure level is approximately equal to the pressure level of blood flowing through the blood flow pathway.

7. The device of claim 1 wherein said one-way pressure relief valve is constructed so that said predetermined pressure level is approximately equal to the pressure level of blood flowing through the blood flow pathway.

8. An oxygenator comprising:
   a tubular shaped housing having first and second open opposite ends being defined by at least a first peripheral wall which defines at least a first passageway therethrough;
   a gas-permeable, liquid-impermeable membrane defined by a plurality of membrane hollow fibers having opposite ends mounted in said tubular housing, said hollow fibers being arranged to position respective open ends adjacent one of said housing open ends, said hollow fibers defining two fluid flow pathways, a first of said pathways being defined through the interior of said fibers, and a second of said pathways being defined about the exterior of said fibers through said housing passageway, one of said pathways being prescribed to carry a flow of oxygen enrichable fluid and the other of said pathways being prescribed to carry an oxygen enriched gas;
   sealing means which is positioned at said housing open ends for fluidally isolating said second pathway and encapsulating and exposing those ends of said fibers adjacent said housing open end;
   first and second cap means fitted to respective ones of said housing ends to form a cavity about said exposed fiber open ends for fluidally isolating said first pathway;
   means defining fluid ports communicating with said pathway;
   at least a first pressure relief valve fitted to said housing which communicates with that one of said pathways carrying said oxygen enriched gas, said valve being a one-way valve constructed to prevent air from passing into the pathway carrying said oxygen enriched gas while allowing gas to vent out of the pathway carrying said oxygen enriched gas when the pressure of said gas reaches a predetermined pressure level.

9. The oxygenator of claim 8 wherein said pressure relief valve is structured so that said predetermined pressure is about 5 mm Hg.

10. The oxygenator of claim 9 wherein said pressure relief valve includes a flap means fitted to a side of said housing, with said housing side further defining at least a first aperture communicating with said gas carrying pathway, and wherein said flap means is formed with a first portion which is affixed to said housing side and a second portion having a resiliently deflectable flap normally covering said aperture when said gas pressure is below 5 mm Hg, and which flap is resiliently moved away from said aperture when said gas pressure exceeds 5 mm Hg.

11. The oxygenator of claim 9 wherein said pressure relief valve is an umbrella valve having a canopy, said umbrella valve being affixed to said housing peripheral side wall to position said umbrella valve canopy outside said housing, said housing further defining one or more apertures formed through said peripheral side wall at a location to lie underneath said canopy.

12. The oxygenator of claim 8 wherein said pressure relief valve is structured so that said predetermined pressure is in the range of about 7 mm Hg to about 16 mm Hg.

13. The oxygenator of claim 12 wherein said pressure relief valve is an umbrella valve having a canopy, said umbrella valve being affixed to said housing peripheral side wall to position said umbrella valve canopy outside said housing, said housing further defining one or more apertures formed through said peripheral side wall at a location to lie underneath said canopy.

14. The oxygenator of claim 13 wherein said canopy is formed with a thickness of at least about 0.008 inches.

15. The oxygenator of claim 14 further including a heat exchange unit connected in series with said housing for regulating the temperature of the oxygen enrichable fluid flowing through said hollow fibers.

16. The oxygenator of claim 13 wherein said canopy is formed with a thickness from about 0.008 inches to about 0.017 inches.

17. The oxygenator of claim 16 further including a heat exchange unit connected in series with said housing for regulating the temperature of the oxygen enrichable fluid flowing through said hollow fibers.

18. The device of claim 8 wherein said one-way pressure relief valve is constructed so that said predetermined pressure level is below the pressure level of blood flowing through the blood flow pathway.

19. In an extracorporeal blood oxygenation device having a housing with separate blood and gas flowpaths formed therein, the improvement comprising:
  a one-way pressure relief valve positioned on the gas flowpath;
  said one-way pressure relief valve being constructed so as to remain closed when the gas pressure within the gas flow pathway is below a predetermined pressure level but to open when the gas pressure within the gas flow pathway is above said predetermined pressure level.

20. The device of claim 19 wherein said one-way pressure relief valve is constructed so that said predetermined pressure level is below the pressure level of blood flowing through the blood flow pathway.

21. The device of claim 19 wherein said one-way pressure relief valve is constructed so that said predetermined pressure level is approximately equal to the pressure level of blood flowing through the blood flow pathway.

22. The device of claim 19 wherein said one-way pressure relief valve comprises:
  means defining an aperture formed in the housing of the blood oxygenation device communicating with the gas flow pathway therein; and
  a resiliently deflectable flap positioned over said aperture, said flap being constructed to lie against the housing when the gas pressure within the gas flow pathway is below said predetermined temperature and to move away from the housing when the pressure within the gas flow pathway exceeds said predetermined pressure.

* * * * *